United States Patent [19]

Yokota et al.

[11] Patent Number: 5,258,541
[45] Date of Patent: Nov. 2, 1993

[54] PROCESS FOR PRODUCING CARBONIC ACID ESTER

[75] Inventors: Shigeru Yokota; Yasutaka Tanaka; Hiroto Miyake, all of Hyogo, Japan

[73] Assignee: Daicel Chemical Industries, Ltd., Sakai, Japan

[21] Appl. No.: 844,982

[22] Filed: Feb. 27, 1992

Related U.S. Application Data

[63] Continuation of Ser. No. 425,173, Oct. 13, 1989, abandoned.

[30] Foreign Application Priority Data

Feb. 16, 1988 [JP] Japan .................................. 33572/88
Jan. 4, 1989 [JP] Japan .................................. 202/89

[51] Int. Cl.$^5$ .............................................. C07C 69/96
[52] U.S. Cl. .................................. 558/260; 558/274; 558/277

[58] Field of Search ..................... 558/260, 274, 277

[56] References Cited

U.S. PATENT DOCUMENTS 4,785,130 11/1988 Bhattacharya ..................... 558/277

FOREIGN PATENT DOCUMENTS 0090977 10/1983 European Pat. Off. .
WO87/07601 12/1987 PCT Int'l Appl. ................. 558/277

*Primary Examiner*—José G. Dees
*Assistant Examiner*—Dwyane C. Jones
*Attorney, Agent, or Firm*—Flynn, Thiel, Boutell & Tanis

[57] ABSTRACT

A carbonic acid ester is produced by reacting an alcohol with carbon monoxide and oxygen in the presence of a catalyst comprising a cupric salt of a weak acid and/or a cupric halide and an alkaline earth metal salt of a weak acid and/or an alkaline earth metal halide.

14 Claims, No Drawings

PROCESS FOR PRODUCING CARBONIC ACID ESTER

This application is a continuation of U.S. Ser. No. 07/425 173, filed Oct. 13, 1989, now abandoned.

The invention relates to a process for producing a carbonic acid ester by reacting an alcohol with carbon monoxide and oxygen with a catalyst. The carbonic acid esters are industrially quite important compounds which are used as intermediates in the production of polymers, medicines and pesticides and also as solvents.

Background of the Invention

Proposed processes for the production of carbonic acid esters include, for example, a process wherein an alcohol is reacted with carbon monoxide and oxygen in the presence of a catalyst which comprises a cuprous halide and an alkali metal halide or alkaline earth metal halide (cf. Japanese Patent Publication No. 8020/1981) and a process wherein an alcohol is reacted with carbon monoxide and oxygen in the presence of a copper compound or a combination of a copper compound with a platinum group compound, an alkali metal salt, etc. (cf. Japanese Patent Publication No. 8816/1986).

However, the former process has a problem in that the velocity of forming the carbonic acid ester is extremely low and the latter process has a problem in that the erosion of the equipment and piping of the plant occurs due to a poor solubility of the catalyst components.

DISCLOSURE OF INVENTION

Therefore, an object of the present invention is to provide a process for producing a carbonic acid ester in an advantageous manner by increasing the velocity of forming the ester while using a catalyst which is as homogeneous as possible.

After intensive investigations made for the purpose of solving the above-described problems, the inventors have found that when a particular catalyst comprising a cupric salt and an alkaline earth metal salt is used in the production of a carbonic acid ester, a high solubility of copper can be obtained, the catalyst is homogeneously dissolved in the reaction solution and the formation velocity is increased. The present invention has been completed on the basis of these findings.

Thus the present invention provides a process for producing a carbonic acid ester by reacting an alcohol with carbon monooxide and oxygen in the presence of a cupric salt or a combination of a cupric salt with a platinum group compound and an alkaline earth metal salt, characterized in that the cupric salt is a weak acid salt and/or a halide and the alkaline earth metal salt is also a weak acid salt and/or a halide.

The catalyst comprises, for example, a combination of (a) a cupric salt of a weak acid with (b) an alkaline earth metal halide or a combination of (a) a cupric salt of a weak acid and a platinum group compound with (b) an alkaline earth metal halide.

Among the catalysts used in the present invention, the cupric salts include, for example, cupric carboxylates such as cupric acetate, pivalate and benzoate; cupric salts of weak acids such as hydrobromic acid, carbonic acid and phenols, e.g. phenol, cresol and p-chlorophenol; and cupric halides such as cupric chloride and bromide. The amount of the cupric salt used is 1 to 3,000 mmol, preferably 10 to 1,000 mmol, per liter of the alcohol.

The alkaline earth metal compounds usable together with the cupric salt include, for example, chlorides, iodides and acetates of beryllium, magnesium, calcium and barium. The amount of the alkaline earth metal compound is preferably 1/10 to 10 mol per mol of the cupric salt. It is particularly preferred that the atomic ratio of the halogen to copper in the catalyst system is higher than $\frac{1}{4}$ and lower than 2.

The platinum group compound used as the catalyst component includes, for example, a halide, acetate and nitrate of ruthenium, rhodium or palladium. Among them, the palladium salt is preferred. The amount of the platinum group compound used is at most 1 mol, preferably at most 1/10 mol, per mole of the cupric salt.

The alcohols used as the reactant in the present invention include, for example, saturated aliphatic alcohols such as methanol and ethanol; unsaturated aliphatic alcohols such as allyl alcohol; aromatic alcohols such as phenol; diols; and polyols. Among them, alcohols having 1 to 20 carbon atom are preferred and methanol is particularly preferred.

Carbon monoxide and oxygen, which are gaseous reactants, are not limited to having a high purity and may be diluted with an inert gas such as nitrogen, argon or carbon dioxide. Therefore, air can be used as the oxygen source.

The reaction of the present invention is conducted in the presence of the above-described catalyst under atmospheric or elevated pressure, preferably 1 to 100 atm. When the gas inert to a reaction is used for dilution, the partial pressures of carbon monoxide and oxygen are adjusted in the ranges of 0.1 to 30 atm and 0.05 to 10 atm, respectively. The reaction temperature ranges from 20° to 250° C. This reaction can be conducted either batchwise or continuously.

It will be understood from the above description that according to the process of the present invention, the velocity of forming the carbonic acid ester by reacting an alcohol with carbon monoxide and oxygen is increased in the presence of the catalyst comprising the cupric salt and the selectivity toward the intended product is increased as compared with those obtained when an ordinary catalyst comprising a cuprous halide is used. Therefore, when the process of the present invention is employed for the production of a carbonic acid ester, the production time can be reduced and the yield of the product can be remarkably increased. Another great advantage of the present invention is that the erosion of the equipment and piping of the plant can be controlled, since the catalyst is homogeneously dissolved in the reaction solution.

EXAMPLES

The following Examples will further illustrate the present invention, but by no means limit the invention.

EXAMPLE 1

DMC (dimethyl carbonate) was produced in a 380 ml autoclave coated with TEFLON 40 ml of a solution of 7.5 mmol/l of palladium chloride, 187.5 mmol/l of cupric acetate and 187.5 mmol/l of magnesium chloride in methanol was used as the catalyst. The catalyst was placed in the autoclave and then 12.0 kg/cm$^2$ of a gaseous mixture comprising 47.5 vol. % of nitrogen, 30 vol. % of carbon monoxide and 22.5 vol. % of argon/oxygen (oxygen content: 33.0 vol. %) was introduced thereinto. The temperature in the autoclave was elevated to 130° C. and the reaction was conducted for 1 h. After the completion of the reaction, the autoclave was cooled and the amounts of carbon monoxide, oxygen, carbon dioxide and formed DMC were determined by gas chromatography. The results are shown in Table 1.

COMPARATIVE EXAMPLE 1

The reaction was conducted in the same manner as that of Example 1 except that cupric acetate used as the catalyst was replaced with cuprous chloride. The products were determined by gas chromatography. The results are shown in Table 1.

EXAMPLE 2

The reaction was conducted in the same manner as that of Example 1 except that 187.5 mmol/l of cupric acetate and 187.5 mmol/l of magnesium chloride were used as the catalyst. The products were determined to obtain the results shown in Table 1.

COMPARATIVE EXAMPLE 2

The reaction was conducted in the same manner as that of Example 2 except that cupric acetate was replaced with cuprous chloride as the catalyst. The results are shown in Table 1.

TABLE 1

| | Catalyst composition (mmol/l) | | | | Amount of formed DMC | Selectivity toward DMC |
|---|---|---|---|---|---|---|
| | PdCl$_2$ | Cu(OAc)$_2$ | CuCl | MgCl$_2$ | (mmol) | S(CO$_2$-DMC) (%) |
| Example 1 | 7.5 | 187.5 | | 187.5 | 9.9 | 32 |
| Comp. Ex. 1 | 7.5 | | 187.5 | 187.5 | 4.9 | 14 |
| Example 2 | | 187.5 | | 187.5 | 5.2 | 21 |
| Comp. Ex. 2 | | | 187.5 | 187.5 | 3.7 | 14 |

Selectivity toward DMC:

$$S(CO_2-DMC) = \frac{(\text{Amount of formed DMC})}{(\text{Amount of formed DMC}) + (\text{Amount of formed } CO_2)} \times 100$$

It is apparent from the results shown in Table 1 that when cupric acetate was used in place of cuprous chloride, the velocity of forming the carbonic acid ester was increased and the selectivity toward the carbonic acid ester was also increased and that when the palladium compound was used together with the copper salt, the amount of formed DMC and the selectivity were increased.

EXAMPLE 3

The reaction was conducted in the same manner as that of Example 1 except that 19.4 kg/cm$^2$ of a gaseous mixture comprising 63.0 vol. % of nitrogen, 27.8 vol. % of carbon monoxide and 27.8 vol. % of argon/oxygen (oxygen content: 33.0 vol. %) was used. The products were determined by gas chromatography. The results are shown in Table 2. The solubility of Cu determined after the completion of the reaction is also shown therein.

COMPARATIVE EXAMPLE 3

The reaction was conducted in the same manner as that of Example 3 except that magnesium chloride was replaced with sodium chloride as the catalyst. The results are shown in Table 2.

COMPARATIVE EXAMPLE 4

The reaction was conducted in the same manner as that of Example 3 except that magnesium chloride was replaced with potassium as the catalyst. The results are shown in Table 2.

TABLE 2

| | Catalyst composition (mmol/l) | | | | | Amount of formed DMC | Selectivity toward DMC | Solubility of Cu |
|---|---|---|---|---|---|---|---|---|
| | PdCl$_2$ | Cu(OAc)$_2$ | MgCl$_2$ | NaCl | KCl | (mmol) | S(CO$_2$-DMC) (%) | (%) |
| Example 3 | 7.5 | 187.5 | 187.5 | | | 9.9 | 13.0 | 39.0 | 100 |
| Comp. Ex. 3 | 7.5 | 187.5 | | 187.5 | | 15.2 | 46.6 | 39 |
| Comp. Ex. 4 | 7.5 | 187.5 | | | 187.5 | 8.9 | 26.5 | 28 |

Selectivity toward DMC:

$$S(CO_2-DMC) = \frac{(\text{Amount of formed DMC})}{(\text{Amount of formed DMC}) + (\text{Amount of formed } CO_2)} \times 100$$

It is apparent from the results shown in Table 2 that in Example 3 where the reaction pressure was higher than that of Example 1, the solubility of copper in the reaction solution was higher, the amount of formed DMC was larger and the selectivity was higher than that of Example 3. It is also apparent that when magnesium chloride was replaced with sodium chloride or potassium chloride, the catalyst system was heterogeneous due to the poor solubility of the catalyst and erosion of the equipment and piping of the plant occurred. Namely, in Example 3, the solubility of copper was higher than that of Comparative Example 3 or 4 and it homogeneously dissolved in the reaction solution and, therefore, the erosion of the equipment and piping of the plant could be controlled.

EXAMPLE 4

38 ml of a 40 wt. % solution of DMC in methanol and a catalyst system comprising 0.17 mmol/l of palladium chloride, 19 mmol/l of copper acetate, 12.7 mmol/l of magnesium acetate and 6.3 mmol/l of magnesium chloride were placed in a 320-ml autoclave lined with glass. Then 12 kg/cm$^2$ of a gaseous mixture comprising 77.5 vol. % of nitrogen, 15 vol. % of carbon monoxide and 7.5 vol. % of oxygen was introduced thereinto. The temperature in the autoclave was elevated to 130° C. and the reaction was conducted for 1 h. After the completion of the reaction, the autoclave was cooled and the amounts of carbon monoxide, oxygen, carbon dioxide and formed DMC were determined by gas chromatography. The results are shown in Table 3.

EXAMPLE 5

The reaction was conducted in the same manner as that of Example 4 except that 0.17 mmol/l of palladium chloride, 4.7 mmol/l of cupric acetate, 14.3 mmol/l of cupric chloride and 19 mmol/l of magnesium acetate were used as the catalyst components. The products were determined by gas chromatography. The results are shown in Table 3.

EXAMPLE 6

The reaction was conducted in the same manner as that of Example 4 except that 0.17 mmol/l of palladium chloride, 6.3 mmol/l of cupric acetate, 12.7 mmol/l of cupric chloride and 19 mmol/l of magnesium acetate were used as the catalyst components. The products were determined by gas chromatography. The results are shown in Table 3.

EXAMPLE 7

The reaction was conducted in the same manner as that of Example 4 except that 0.17 mmol/l of palladium chloride, 9.5 mmol/l of copper acetate, 9.5 mmol/l of cupric chloride and 19 mmol/l of magnesium acetate were used as the catalyst components. The products were determined by gas chromatography. The results are shown in Table 3.

EXAMPLE 8

The reaction was conducted in the same manner as that of Example 4 except that 0.17 mmol/l of palladium chloride, 12.7 mmol/l of copper acetate, 6.3 mmol/l of cupric chloride and 19 mmol/l of magnesium acetate were used as the catalyst components. The products were determined by gas chromatography. The results are shown in Table 3.

EXAMPLE 9

The reaction was conducted in the same manner as that of Example 4 except that 0.17 mmol/l of palladium chloride, 19 mmol/l of copper acetate and 19 mmol/l of magnesium chloride were used as the catalyst components. The products were determined by gas chromatography. The results are shown in Table 3.

Selectivity toward DMC:

$$S(CO-DMC) = \frac{\text{Amount of formed DMC (mol)}}{\text{Amount of consumed CO (mol)}} \times 100$$

$$S(CO_2-DMC) = \frac{r(DMC)}{r(DMC) + r(CO_2)} \times 100$$

It is apparent from the results shown in Table 3 that the DMC-forming activities observed in Examples 4 to 9 were higher than those observed in Comparative Examples 1 and 2 as shown in Table 1. Further it will be understood that when a catalyst having an atomic ratio of halogen to copper in the range of ¼ to 2 was used, the selectivity toward DMC was remarkably increased in addition to the DMC-forming activity.

EXAMPLE 10

DMC was produced in a 380-ml autoclave coated with Teflon. A solution of 0.34 mmol/l of palladium chloride, 38 mmol/l of copper acetate and 19 mmol/l of magnesium chloride in methanol containing 10 wt. % DMC was fed to the reactor. The reaction temperature was 130° C. 5 vol. % of carbon monoxide, 2.5 vol. % of oxygen and carbon dioxide as the diluent were used. The total pressure was 20 kg/cm². The DMC-forming activity and the selectivity toward DMC were determined by gas chromatography after the stationary state was realized. The results are shown in Table 4.

EXAMPLE 11

The reaction was conducted in the same manner as that of Example 10 except that 0.34 mmol/l of palladium chloride, 19 mmol/l of copper acetate, 19 mmol/l of cupric chloride and 38 mmol/l of magnesium acetate were used as the catalyst components. The products were determined by gas chromatography. The results are shown in Table 4.

EXAMPLE 12

The reaction was conducted in the same manner as that of Example 10 except that 0.34 mmol/l of palladium chloride, 38 mmol/l of cupric acetate and 38 mmol/l of magnesium chloride were used as the catalyst components. The products were determined by gas chromatography. The results are shown in Table 4.

TABLE 4

| | Catalyst composition (mmol/l) | | | | | Activity (mol/l · h) | Selectivity (%) |
|---|---|---|---|---|---|---|---|
| | PdCl$_2$ | Cu(OAc)$_2$ | CuCl$_2$ | Mg(OAc)$_2$ | MgCl$_2$ | r(DMC) | S(CO$_2$-DMC) |
| Example 10 | 0.34 | 38 | | | 19 | 1.177 | 43.4 |
| Example 11 | 0.34 | 19 | 19 | 38 | | 1.211 | 47.1 |
| Example 12 | 0.34 | 38 | | | 38 | 0.742 | 49.4 |

TABLE 3

| | Catalyst composition (mmol/l) | | | | | Activity (mol/l · h) | | Selectivity (%) |
|---|---|---|---|---|---|---|---|---|
| | PdCl$_2$ | Cu(OAc)$_2$ | CuCl$_2$ | Mg(OAc)$_2$ | MgCl$_2$ | r(DMC) | r(CO$_2$) | S(CO$_2$-DMC) |
| Example 4 | 0.17 | 19 | | 12.7 | 6.3 | 0.154 | 0.046 | 77.2 |
| Example 5 | 0.17 | 4.7 | 14.3 | 19 | | 0.255 | 0.067 | 79.3 |
| Example 6 | 0.17 | 6.3 | 12.7 | 19 | | 0.202 | 0.057 | 78.0 |
| Example 7 | 0.17 | 9.5 | 9.5 | 19 | | 0.249 | 0.080 | 75.8 |
| Example 8 | 0.17 | 12.7 | 6.3 | 19 | | 0.184 | 0.052 | 77.8 |
| Example 9 | 0.17 | 19 | | | 19 | 0.143 | 0.089 | 61.7 |

Selectivity toward DMC:

It is apparent from the results shown in Table 4 that the DMC-forming activity can be remarkably improved when the atomic ratio of the halogen to copper is reduced by merely reducing the amount of magnesium chloride in the catalyst. It is apparent also that the DMC-forming activity can be remarkably increased when the atomic ratio of halogen to copper is reduced by using palladium chloride, cupric acetate, cupric chloride and magnesium acetate. Namely, the DMC-forming activity can be remarkably improved when a catalyst having an atomic ratio of halogen to copper of higher than ¼ and lower than 2 is used.

It will be apparent from the above description that the atomic ratio of halogen to copper in the catalyst is particularly preferably higher than ¼ and lower than 2.

We claim:

1. In a process for producing a carbonic acid ester by reacting an alcohol with carbon monoxide and oxygen in a liquid phase reaction, the improvement comprising said reaction being conducted in the presence of a catalyst comprising a cupric salt, an alkaline earth metal salt and a platinum group compound, said cupric salt beign a weak acid salt and/or a halide and said alkaline earth metal salt being a weak acid salt and/or a halide, the atomic ratio of halogen to copper in the catalyst being higher than ¼ and lower than about 2.

2. A process according to claim 1, wherein the reaction is conducted in the presence of a catalyst comprising:
   (a) a cupric salt of a weak acid and
   (b) an alkaline earth metal halide.

3. A process according to claim 1, wherein the catalyst further comprises a platinum group compound.

4. A process for producing a carbonic acid ester as claimed in claim 3, wherein the platinum group compound is a palladium compound, the cupric salt is cupric acetate and/or a cupric halide and the alkaline earth metal salt is an alkaline earth metal acetate and/or halide.

5. A process according to claim 3 characterized in that the reaction is conducted in the presence of a catalyst comprising:
   (a) a cupric salt of a weak acid and a platinum group compound, and
   (b) an alkaline earth metal halide.

6. A process according to claim 1, wherein the catalyst comprises a cupric salt of a halide, a platinum group compound and an alkaline earth metal salt of a weak acid.

7. A process according to claim 1, wherein the alkaline earth metal salt is magnesium acetate and/or halide.

8. A process according to claim 1, wherein the partial pressure of carbon monoxide is from 0.1–30 atm and the partial pressure of oxygen is from 0.05 to 10 atm.

9. In a process for producing dimethyl carbonate by reacting an alcohol with carbon monoxide and oxygen in a liquid phase reaction, the improvement comprising said reaction being conducted in the presence of a catalyst comprising a cupric salt selected from the group consisting of copper acetate, cupric chloride and mixtures thereof, an alkaline earth metal salt selected from the group consisting of magnesium acetate, magnesium chloride and mixtures thereof and a platinum group compound, the atomic ratio of halogen to copper in the catalyst being higher than ¼ and lower than about 2.

10. A process according to claim 9, wherein said catalyst comprises palladium chloride as the platinum group compound.

11. A process according to claim 9, wherein the partial pressure of carbon monoxide is from 0.1–30 atm and the partial pressure of oxygen is from 0.05 to 10 atm.

12. In a process for producing a carbonic acid ester by reacting an alcohol and carbon monoxide and oxygen in a liquid phase reaction, the improvement comprising said reaction being conducted in the presence of a catalyst consisting essentially of a cupric salt, an alkaline earth metal salt and a platinum group compound, said cupric salt being selected from the group consisting of a weak acid salt, a halide selected from the group consisting of cupric chloride, cupric bromide and mixtures thereof, and said alkaline earth metal salt being a weak acid salt and/or a halide, the atomic ratio of halogen to copper in the catalyst being higher than ¼ and lower than about 2.

13. A process according to claim 1, wherein the cupric halide salt is selected from the group consisting of cupric chloride, cupric bromide and mixtures thereof.

14. A process according to claim 12, wherein said catalyst consists essentially of cupric acetate, cupric chloride, said alkaline earth metal salt and said platinum group compound.

* * * * *

UNITED STATES PATENT AND TRADEMARK OFFICE
CERTIFICATE OF CORRECTION

PATENT NO. : 5 258 541
DATED : November 2, 1993
INVENTOR(S) : Shigeru Yokota et al It is certified that error appears in the above-identified patent and that said Letters Patent is hereby corrected as shown below:

```
Column 7, line 20;   change "beign" to ---being---.
Column 7, line 24;   change "1/4" to ---1/2---.
Column 8, line 18;   change "1/4" to ---1/2---.
Column 8, line 36;   change "1/4" to ---1/2---.
```

Signed and Sealed this

Seventeenth Day of May, 1994

Attest:

BRUCE LEHMAN

*Attesting Officer*    *Commissioner of Patents and Trademarks*